United States Patent
Somani et al.

(10) Patent No.: US 7,478,907 B2
(45) Date of Patent: *Jan. 20, 2009

(54) PRESBYOPIA CORRECTION THROUGH NEGATIVE HIGH-ORDER SPHERICAL ABERRATION

(75) Inventors: Seema Somani, Milpitas, CA (US); Kingman Yee, San Jose, CA (US)

(73) Assignee: AMO Manufacturing USA, LLC, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,147

(22) Filed: Jul. 19, 2007

(65) Prior Publication Data

US 2008/0015461 A1     Jan. 17, 2008

Related U.S. Application Data

(63) Continuation of application No. 11/173,904, filed on Jun. 30, 2005, now Pat. No. 7,261,412.

(51) Int. Cl.
    *G02C 7/02*     (2006.01)
    *A61F 2/16*     (2006.01)

(52) U.S. Cl. .................. 351/177; 351/159; 351/160 R; 623/6.11; 606/4

(58) Field of Classification Search .................. 351/177
See application file for complete search history.

(56) References Cited

U.S. PATENT DOCUMENTS 6,045,578 A * 4/2000 Collins et al. ................ 623/4.1
7,261,412 B2 * 8/2007 Somani et al. ............... 351/177
2004/0237971 A1 * 12/2004 Radhakrishnan et al. .... 128/898
2005/0041203 A1 * 2/2005 Lindacher et al. ........... 351/168
2005/0203619 A1 * 9/2005 Altmann .................... 623/6.23
2005/0259221 A1 * 11/2005 Marmo .................... 351/160 R
2006/0158611 A1 * 7/2006 Piers et al. .................. 351/177

FOREIGN PATENT DOCUMENTS

WO     WO 2004/052253     *     6/2004

* cited by examiner

*Primary Examiner*—Jordan M. Schwartz
(74) *Attorney, Agent, or Firm*—Townsend and Townsend and Crew LLP

(57) ABSTRACT

Devices, systems, and methods for treating and/or determining appropriate prescriptions for one or both eyes of a patient are particularly well-suited for addressing presbyopia, often in combination with concurrent treatments of other vision defects. High-order spherical aberration may be imposed in one or both of a patient's eyes, often as a controlled amount of negative spherical aberration extending across a pupil. A desired presbyopia-mitigating quantity of high-order spherical aberration may be defined by one or more spherical Zernike coefficients, which may be combined with Zernike coefficients generated from a wavefront aberrometer. The resulting prescription can be imposed using refractive surgical techniques such as laser eye surgery, using intraocular lenses and other implanted structures, using contact lenses, using temporary or permanent corneal reshaping techniques, and/or the like.

12 Claims, 10 Drawing Sheets

|  | Radius (mm) | Conic Const | 2nd order coef | 4th order coef | 6th order coef | 8th order coef |
|---|---|---|---|---|---|---|
| Basic | 7.8 | -0.5 | 0 | 0 | 0 | 0 |
| Optimized | 7.71 | -0.5 | -0.000816 | 0.000825 | -0.000231 | 0.000019 |

FIG. 10

|  | Infinity | 10 m | 4 m | 1 m | 0.6 m |
|---|---|---|---|---|---|
| Basic | 0.4 | 0.4 | 0.3 | 0.14 | 0.06 |
| Basic with +1D spectacle | 0.015 | 0.015 | 0.04 | 0.4 | 0.04 |
| Optimized | 0.08 | 0.13 | 0.19 | 0.39 | 0.14 |

FIG. 11

PRESBYOPIA CORRECTION THROUGH NEGATIVE HIGH-ORDER SPHERICAL ABERRATION

CROSS REFERENCES TO RELATED APPLICATIONS

This is a continuation application of U.S. patent application Ser. No. 11/173,904 filed Jun. 30, 2005, the disclosure of which is incorporated herein by reference.

BACKGROUND OF THE INVENTION

This invention relates to optical correction, and in particular provides methods, devices, and systems for treating presbyopia and other vision conditions, for developing prescriptions for treatment of presbyopia and other vision conditions, and/or the like.

Presbyopia is a condition that affects the accommodation properties of the eye. As objects move closer to a young, properly functioning eye, ciliary muscle contraction and zonular relaxation may allow the lens of the eye to become rounder or more convex, and thus increase its optical power and ability to focus at near distances. Accommodation can allow the eye to focus and refocus between near and far objects.

Presbyopia normally develops as a person ages, and is associated with a natural progressive loss of accommodation. The presbyopic eye can lose the ability to rapidly and easily refocus on objects at varying distances. There may also be a loss in the ability to focus on objects at near distances. Although the condition progresses over the lifetime of an individual, the effects of presbyopia usually become noticeable after the age of 45 years. By the age of 65 years, the crystalline lens has often lost almost all elastic properties and has only limited ability to change shape.

To address the vision problems associated with presbyopia, reading glasses have traditionally been used by individuals to thus allow the eye to focus on near objects and maintain a clear image. This approach is similar to that of treating hyperopia, or farsightedness.

Presbyopia has also been treated with a number of alternative approaches. Many presbyopes are prescribed bi-focal eyeglasses, where one portion of the lens is corrected for distance vision and another portion of the lens is corrected for near vision. When peering down through the bifocals, the individual looks through the portion of the lens corrected for near vision. When viewing distant objects, the individual looks higher, through the portion of the bi-focals corrected for distance vision. Contact lenses and intra-ocular lenses (IOLs) have also been used to treat presbyopia, for example, by relying on monovision (where one eye is corrected for distance-vision, while the other eye is corrected for near-vision) or bilateral correction with either bi-focal or multi-focal lenses. In the field of refractive surgery, ablation profiles have been suggested to treat presbyopia, often with the goal of passively increasing the range of focus of the eye.

While the known and proposed methods for treatment of presbyopia have had varying degrees of success, none has proven to be ideal for all patients. In particular, generating prescriptions for extending the range of viewing distances without degrading the patient's vision (and satisfaction with their visual capabilities) can be challenging.

In light of the above, it would be desirable to have improved methods, devices, and systems for treatment of presbyopia. It would be generally desirable for these improved techniques to be compatible with known methods for treating refractive errors of the eye. Ideally, such improved eye treatment approaches might be relatively easy to implement without significantly increasing the complexity or cost for treatment of patients, while increasing the presbyopia treatment efficacy.

BRIEF SUMMARY OF THE INVENTION

The present invention generally provides improved devices, systems, and methods for treating and/or determining appropriate prescriptions for one or both eyes of a patient. The techniques of the present invention are particularly well-suited for addressing presbyopia, often in combination with concurrent treatments of other vision defects. In many embodiments, the techniques of the present invention will intentionally impose high-order spherical aberration in one or both of a patient's eyes. This spherical aberration will often comprise a controlled amount of negative spherical aberration extending across a pupil. Conveniently, the desired presbyopia-mitigating quantity of high-order spherical aberration may be defined by one or more spherical Zernike coefficients. Spherical Zernike coefficients may be readily combined with Zernike coefficients generated from wavefront aberrometers so as to generate a prescription for a patient which both corrects the undesirable aberrations of the eye and provides at least partial relief from presbyopia. The prescription can be imposed on the eye using refractive surgical techniques such as laser eye surgery, using intraocular lenses and other implanted structures, using contact lenses, using temporary or permanent corneal reshaping techniques, and/or the like.

In a first aspect, the invention provides a method for treating presbyopia of a patient having an eye. The method comprises inducing a presbyopia-mitigating quantity of high-order spherical aberration in the eye.

Optionally, the induced spherical aberration may extend across a pupil of the eye. The presbyopia-mitigating quantity may be in a range from about 0.05 to about 0.4 microns, often being in a range from about 0.1 to about 0.3 microns, and ideally being in a range from about 0.15 to about 0.25 microns of negative spherical aberration across the pupil. Typically, the spherical aberration will comprise a radially symmetric asphericity. The spherical aberration can be described by at least one significant radially symmetric high-order Zernike polynomial coefficient, and will typically correspond to a plurality of significant, high-order Zernike polynomial coefficients.

For the purpose of refractive correction of an eye, the spherical aberration may be combined with a plurality of Zernike coefficients corresponding to the wavefront of that eye. The presbyopia-mitigating quantity of spherical aberration and refractive defect-correcting prescription may be combined, with the combination induced in the eye by reshaping a cornea, inserting a lens into the eye, positioning a lens in front of the cornea, laser eye surgery, LASEK, LASIK, photorefractive keratectomy, a contact lens, a scleral lens, an intraocular lens, a phacik intraocular lens, and/or the like.

In some embodiments, refractive aberrations of the eye can be measured with a wavefront aberrometer. Wavefront Zernike coefficients of the measured refractive aberrations may be determined, and a prescription may be defined for the patient by combining the wavefront Zernike coefficients with at least one high-order Zernike coefficient corresponding to the presbyopia-mitigating quantity of spherical aberration.

The image of a point source placed in front of an eye is typically a blurred spot. As the point source moves from a very far distance (optionally defined as mathematical infinity) toward the cornea, the image may be focused behind the retina. As a result, the image formed on the retina may be more blurred. In many embodiments it will be preferable for the treated eye to image a point source as having a relatively intense central spot surrounded by a lower intensity region instead of a lower intensity central spot with a higher intensity ring. In this configuration, the image of a larger object formed on the retina can be sharper as it has more defined edges. Toward that end, the treated eye can be configured such that a far point source results in a focused spot at the retina and a more intense core and a dimmer periphery-type image spot forming at distances between the eye lens and the retina. The treated eye will see objects at a far distance focused on the retina and objects at near distances form relatively sharp images on the retina without employing accommodation. Such an object image on the retina of such an eye can further be focused by utilizing residual accommodation of the eye.

In many embodiments, the presbyopia-mitigating quantity of spherical aberration will be identified, and a presbyopia prescription will be determined so as to provide the identified quantity of spherical aberration. The presbyopia-mitigating quantity of spherical aberration can be induced by superimposing the determined presbyopia prescription on the eye.

In another aspect, the invention provides a method for treating presbyopia in a patient having an eye with a pupil. The method comprises altering a refraction of the eye so that the altered eye has a high-order negative spherical aberration in a range from about 0.1 to about 0.3 microns across the pupil so that the effect of the presbyopia is mitigated.

In another aspect, the invention provides a method for planning a presbyopia treatment for an eye of a patient having a pupil. A plurality of Zernike polynomial coefficients correspond to measured aberrations of the eye. The method comprises deriving a prescription for the eye by combining the Zernike polynomial coefficients with at least one high-order Zernike polynomial coefficient of a presbyopia-mitigating negative spherical aberration.

In yet another aspect, the invention provides a system for treating presbyopia. The system comprises a prescription generator module coupled to an output. The prescription generator module defines a presbyopia-mitigating quantity of high-order spherical aberration for the eye. The output is configured for communication to a lens producing or modifying assembly.

Typically, the prescription generator will have an input coupled to a wavefront system. The wavefront system generates a plurality of refractive Zernike coefficients corresponding to measured aberrations of an eye. The lens producing assembly may also comprise a portion of the system, with an exemplary lens producing assembly including an ablative laser for imposing a prescription on the eye by directing a pattern of laser energy toward a cornea of the eye. The prescription generator may combine the refractive wavefront correction with a presbyopia-mitigating wavefront modification. In some embodiments, the prescription generator may combine the refractive Zernike coefficients with at least one presbyopia-mitigating Zernike coefficient. The at least one presbyopia-mitigating Zernike coefficient may include at least one high-order Zernike coefficient corresponding to the presbyopia-mitigating quantity of spherical aberration. This may provide the eye with between about 0.1 and about 0.3 microns of negative spherical aberration across the eye.

BRIEF DESCRIPTION OF THE DRAWINGS

FIG. 10 is a table showing exemplary shape parameters of basic and treated corneas using Zernike polynomial coefficients to define a desired negative asphericity of the cornea.

FIG. 11 is a table showing modulation transfer function (MTF) values at 50 cycles/mm for differing object distances.

DETAILED DESCRIPTION OF THE INVENTION

The present invention generally provides devices, systems, and methods for treating (and/or planning treatments for) one or both eyes of a patient. The invention provides customized or general presbyopia-mitigating shapes, and embodiments of the present invention can be readily adapted for use with existing laser systems, wavefront measurement systems, and other optical measurement and refractive correction devices, systems, and techniques. While the systems, software, and methods of the present invention are described primarily in the context of a laser eye surgery system, it should be understood the present invention may be adapted for use in alternative eye treatment devices, procedures, and systems such as spectacle lenses, intraocular lenses, contact lenses, corneal ring implants, collagenous corneal tissue thermal remodeling, and the like.

Figure 1:
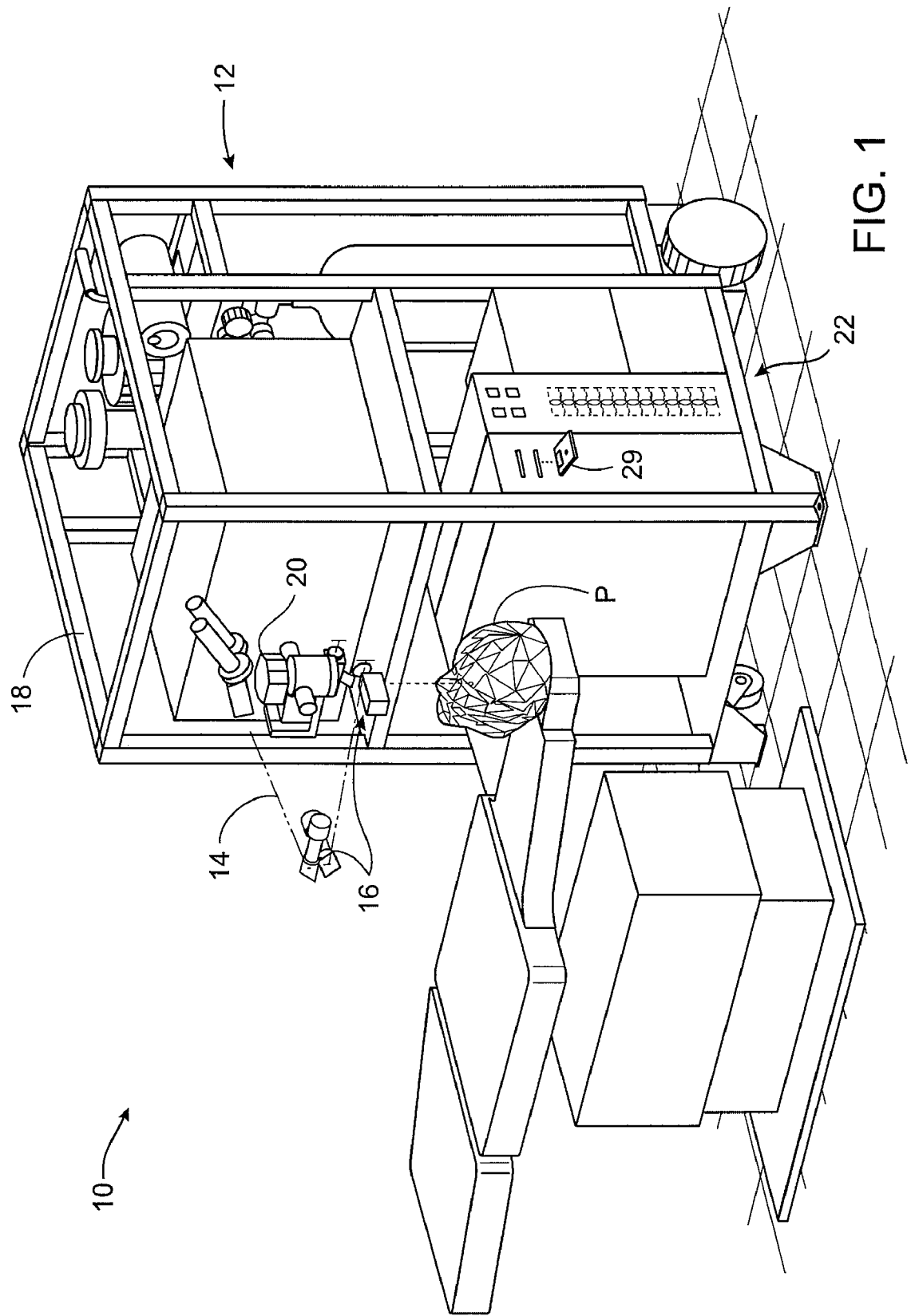
FIG. 1 illustrates a laser ablation system according to an embodiment of the present invention.

Referring now to FIG. 1, a laser eye surgery system 10 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. Embodiments of the present invention may also be useful with alternative sources of ultraviolet or infrared radiation, particularly those adapted to controllably ablate the corneal tissue without causing significant damage to adjacent and/or underlying tissues of the eye. In some alternate embodiments, the laser beam source may employ a solid state laser source having a wavelength between 193 and 215 nm as described in U.S. Pat. Nos. 5,520,679 and 5,144,630 to Lin and U.S. Pat. No. 5,742,626 to Mead, the full disclosures of which are incorporated herein by reference. In other embodiments, the laser source comprises an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used in the present invention.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. Suitable systems also include commercially available refractive laser systems such as those manufactured and/or sold by Alcon, Bausch & Lomb, Nidek, WaveLight™, LaserSight™, Schwind, Zeiss Meditec, and the like.

Figure 2:
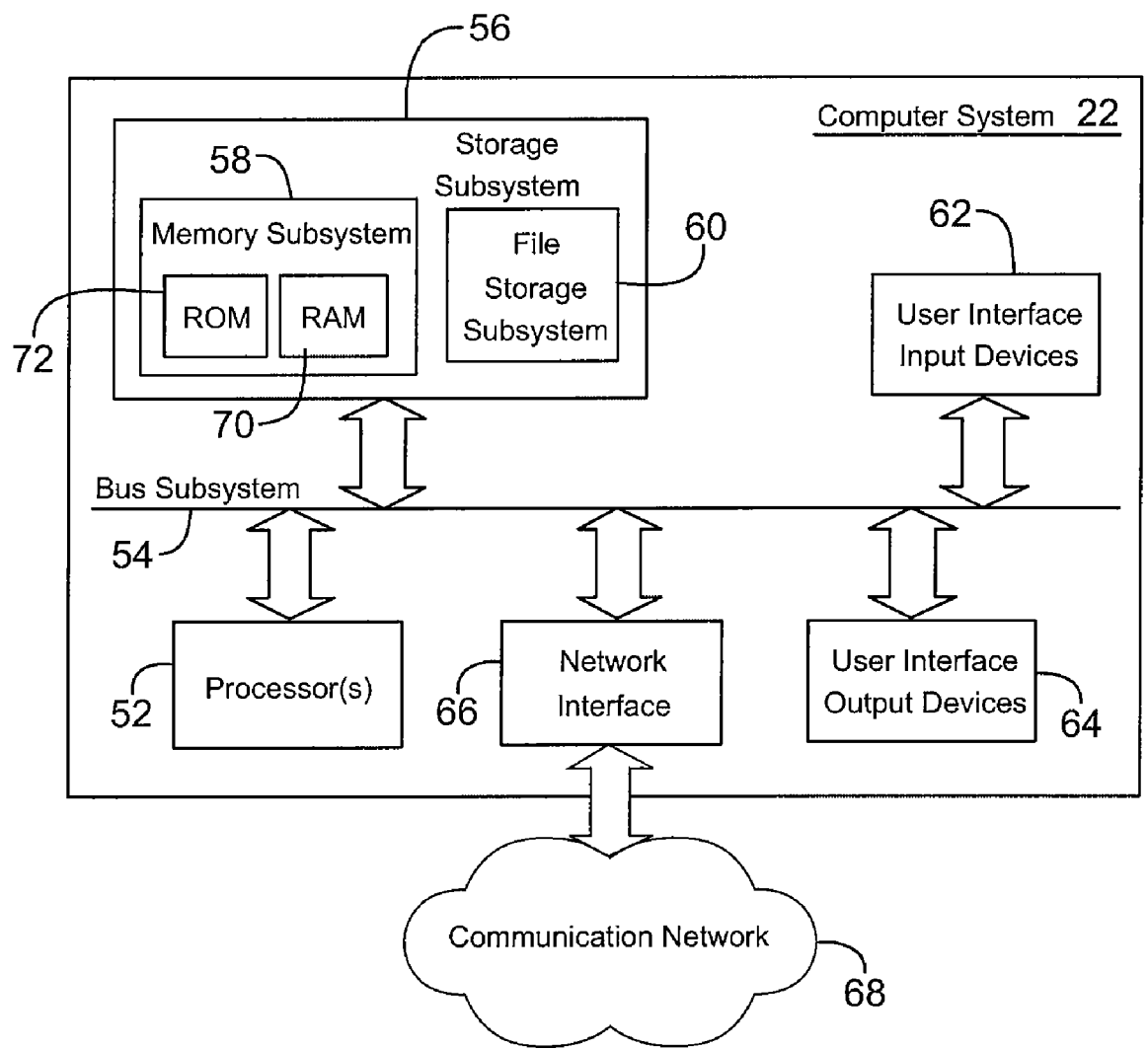
FIG. 2 schematically illustrates a computer system of the laser system of FIG. 1.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods described herein. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 stores the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple buses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 represents only an example for purposes of illustrating one embodiment of the present invention. Many other configurations of computer system 22 are possible having more or less components than the computer system depicted in FIG. 2.

Figure 3:
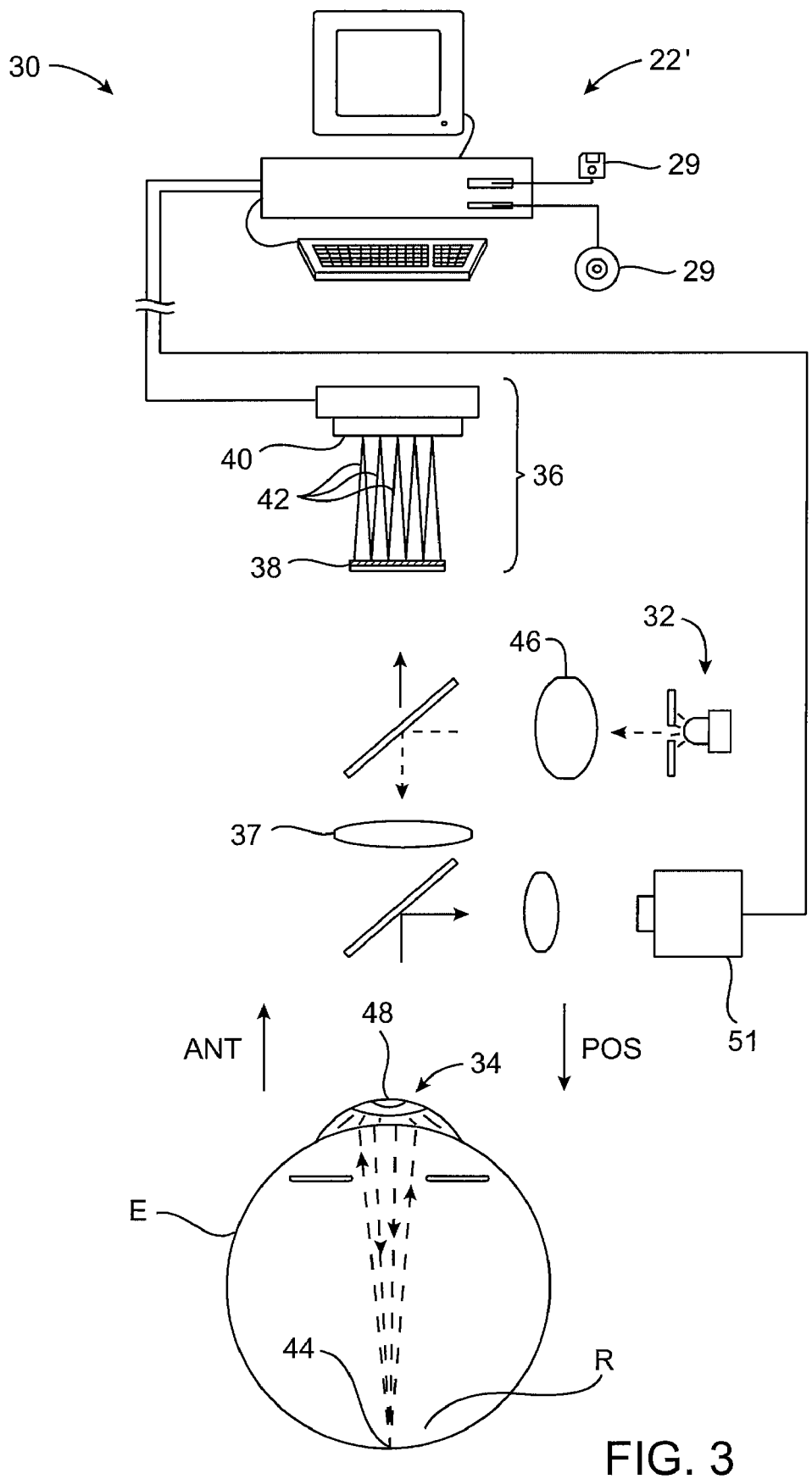
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a wavefront exiting the patient's eye. Devices based on the Hartmann-Shack principle generally include a lenslet array to sample the slopes across the pupil of the eye. Thereafter, the local slopes are analyzed so as to reconstruct the wavefront surface or map, often using Zernike polynomial expansion methods.

More specifically, one wavefront measurement system 30 includes a light source 32, such as a laser, which projects a source image through refractive tissues 34 of eye E so as to form an image 44 upon a surface of retina R. The image from retina R is transmitted by the refractive system of the eye (e.g., refractive tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the computer system components of the wavefront measurement system 30 and laser surgery system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. The reflected light from retina R is transmitted through optical tissues 34 and imaged onto a surface of image sensor 40 and the eye pupil P is similarly imaged onto a surface of lenslet array 38. The lenslet array separates the transmitted light beam into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Light source 32 generally sends light in a posterior orientation through optical tissues 34 onto retina R as indicated in FIG. 3. Optical tissues 34 again transmits light reflected from the retina anteriorly toward wavefront sensor 36. Image 44 actually formed on retina R may be distorted by any imperfections in the eye's optical system when the image source is originally transmitted by optical tissues 34. Optionally, image projection optics 46 may be configured or adapted to decrease any distortion of image 44.

In some embodiments, projection optics 46 may decrease lower order optical errors by compensating for spherical and/or cylindrical errors of optical tissues 34. Higher order optical errors of the optical tissues may also be compensated through the use of an adaptive optics system, such as a deformable mirror. Use of a light source 32 selected to define a point or small spot at image 44 upon retina R may facilitate the analysis of the data provided by wavefront sensor 36. Regardless of the particular light source structure, it will be generally beneficial to have a well-defined and accurately formed image 44 on retina R.

The wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information may include all the available information on the wavefront error of the eye and is typically sufficient to reconstruct the wavefront or a desired portion of it. In such embodiments, there may be no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While embodiments of the invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

Figure 4:
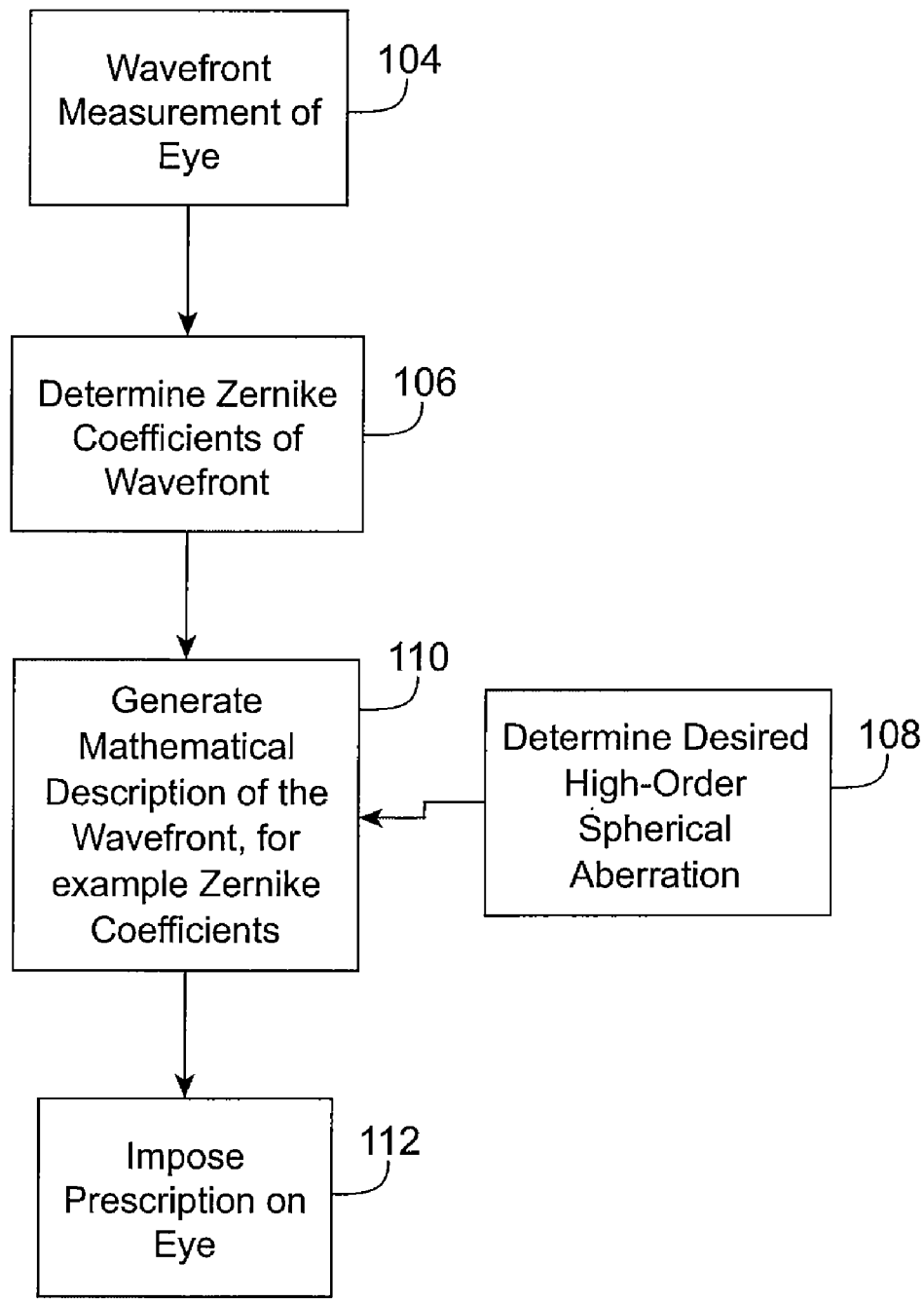
FIG. 4 is a flowchart schematically illustrating a method for mitigating presbyopia by intentionally imposing high-order spherical aberration across a pupil using the laser ablation system of FIG. 1 and the wavefront measurement system of FIG. 3.

Referring now to FIG. 4, a method for treating presbyopia will generally include measurement of a wavefront of an eye using a wavefront sensor, such as that schematically illustrated in FIG. 3. In many embodiments, Zernike coefficients of the wavefront will be determined 106. The wavefront and Zernike coefficients can be used to directly determine a refractive prescription so as to correct optical aberrations of the eye. Known wavefront-based optical corrections often seek to correct or compensate for all optical aberrations of the eye so that the eye is, after treatment, emmetropic.

In exemplary method 102, rather than developing a prescription so as to provide an emmetropic eye, a presbyopia-mitigating high-order spherical aberration is determined 108. This desired spherical aberration, together with the Zernike coefficients from the wavefront, are used to determine a prescription 110, with the prescription generally leaving the treated eye with the desired spherical aberration while correcting other high-order and standard refractive errors. The prescription is then imposed on the eye 112, optionally using a laser eye surgery system such as that illustrated in FIG. 1.

Wavefront measurements may be taken using a variety of commercially available systems, with an exemplary wavefront measurement system comprising a VISX WaveScan™ system, available from VISX, Incorporated of Santa Clara, Calif. Alternative wavefront measurement systems include those described in, for example, U.S. Pat. No. 6,271,915. Still further alternative wavefront measurement systems may be employed, with the preferred systems measuring the wavefront using light which has been transmitted through the refractive tissues of the eye from a retina, as described above.

While exemplary presbyopia-mitigating method 102 determines Zernike coefficients of the wavefront 106, alternative methods may employ any of a variety of alternative mathematical frameworks so as to define the wavefront. For example, direct wavefront-based corneal ablation treatment prescriptions may be derived using methods and systems such as those described in U.S. patent application Ser. No. 10/006, 992, the full disclosure of which is incorporated herein by reference. Wavefront reconstruction using Fournier transformations and direct integration may also be employed, including the techniques described in U.S. patent application Ser. No. 10/872,107, the full disclosure of which is also incorporated herein by reference. Regardless, the wavefront reconstruction will generally correspond to at least some amount of irregular aberration of the eye. By basing a prescription at least in part on such irregular aberrations, the treatments described herein may provide visual acuities of at least 20/20 or better, in some cases providing visual acuities of better than 20/20, often along with presbyopia-mitigation.

A number of approaches may be employed to determine a desired presbyopia-mitigating high-order spherical aberration 108. As used herein, high-order spherical aberration encompasses spherical aberrations other than standard myopia and hyperopia. Desired spherical aberration may be determined based on empirical data, simple or complex models of the refractive tissues, and the like. When the wavefront reconstruction comprises Zernike coefficients, the desired presbyopia-mitigating spherical aberration may conveniently be modeled as radially symmetric Zernike polynomial expansion coefficients, such as terms $Z(2, 0)$, $Z(4, 0)$, $Z(6, 0)$, and the like. In other embodiments, different mathematical formulations of the desired spherical aberration may be employed.

When the wavefront reconstruction 106 and presbyopia-mitigating spherical aberration 108 have been defined using Zernike polynomials, the combined prescription 110 may be directly calculated by superimposing the appropriate asphericity on the eye while otherwise correcting the wavefront error. This can be as easy as adding or subtracting the appropriate polynomial terms to the measured wavefront. Where other reconstruction techniques are employed, or where the desired presbyopia-mitigating spherical aberration is defined in mathematical terms which differ from that of the wavefront reconstruction, more complex analytical approaches for determining the combined prescription may be employed.

Once the desired prescription has been determined 110, that prescription may be imposed on the eye 112 using any of a wide variety of alternative refraction altering approaches. For example, custom contact lenses may be laser ablated or otherwise formed, intraocular or phacik lenses may be shaped by lasers or other sculpting techniques, selective corneal collagen contraction using laser or other heating methodologies may be employed, or the like. Regardless, in many embodiments, the desired spherical aberration will extend across a pupil of the patient after the treatment is complete, and often after any associated healing takes place.

Figure 5:
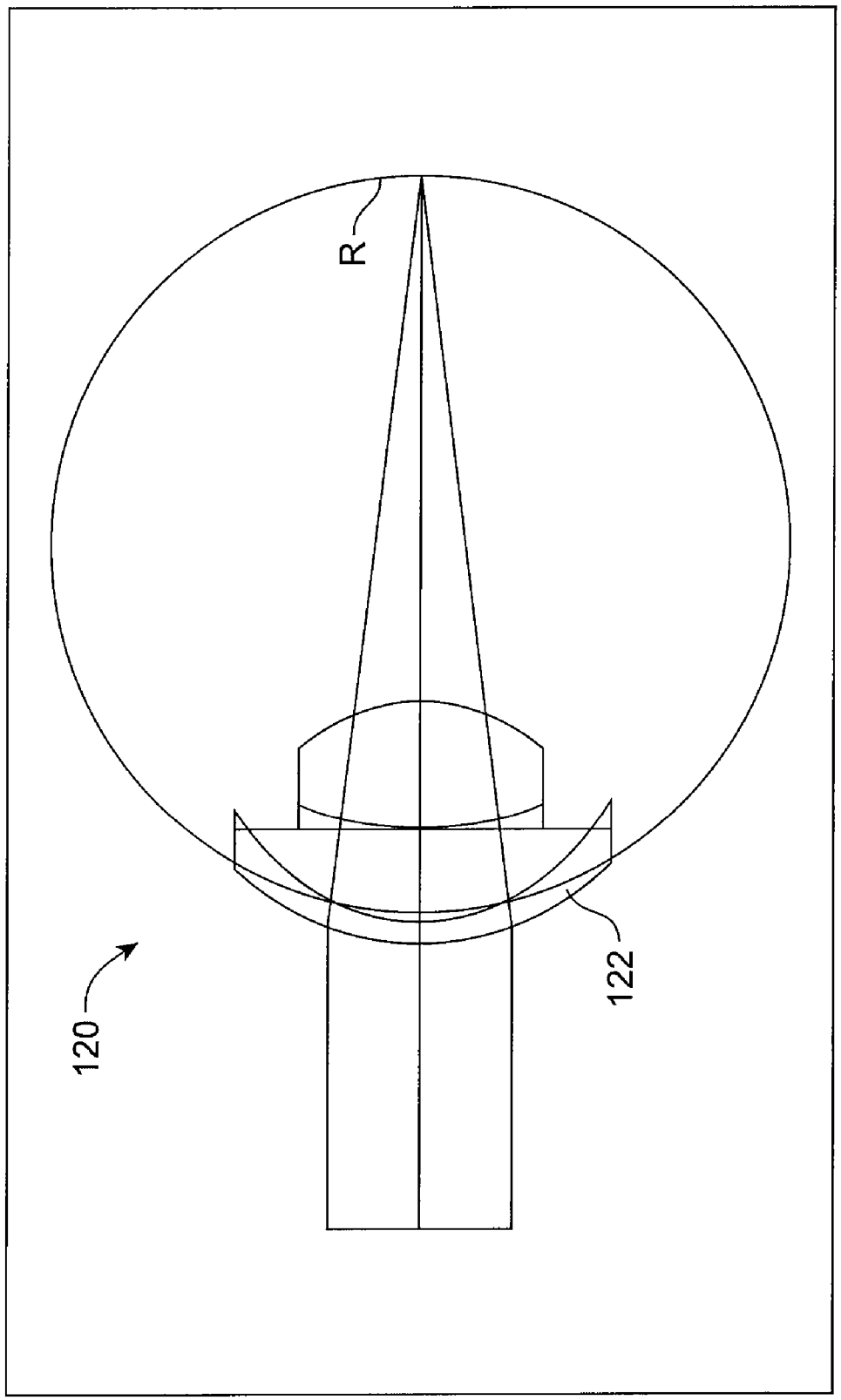
FIG. 5 illustrated an optical model of an eye for use in deriving a desired presbyopia-mitigating spherical aberration for use in one embodiment of the method of FIG. 4.

Addressing how to determine a desired high-order spherical aberration 108 so as to mitigate presbyopia, the human eye generally has multiple refractive elements including a cornea, crystalline lens, and vitreous fluid. An object is seen in focus when a sharp image of that object is formed on the retina R, as schematically illustrated in FIG. 5. The range of distances throughout which an object will appear in focus depends at least in part on accommodation of the crystalline lens. Assuming the accommodation of the lens is small or negligible (which may happen as a person ages) the viewed object will appear blurry as it moves away from a best viewing distance. Changes in image characteristics with changes in viewing distance may also be related to (and may correspond to) changes in the image characteristics with changes in an image focal plane or focal distance anterior of and/or posterior to the retina. The rate at which the object becomes blurry depends on the optical properties of the eye and the pupil diameter. The blurring of the image with changes in focal distance may be reduced by applying an appropriate optical correction to the eye. The desired corrections will generally be described herein as being applied to the cornea using laser ablation, although other refractive treatment modalities may alter refraction anterior to the cornea (such as using a contact lens or scleral lens) or posterior of the cornea (intraocular lenses, or the like).

Spherical aberrations are radially symmetric aberrations of the optical system, and may cause light passing through the different parts of the pupil to focus at different distances from the cornea. Consequently, the image of a point source of light may become a blurred spot, or the like. A relative position of paraxial and peripheral images (as imaged within a central region of the pupil and a peripheral region of the pupil, respectively) along the optical axis may determine a sign of the spherical aberration. When the paraxial focal length of the optical system is shorter than the peripheral focal distance, the spherical aberration has a negative sign, and when the paraxial focal length of the optical system is longer than the peripheral focal distance, the spherical aberration has a positive sign.

Human eyes typically have a small amount of spherical aberration, as will generally be identified in wavefront measurements of the eye 104. Post-surgical eyes and/or pathological eyes may have significant quantities of spherical aberration. Retinal image quality may depend on both the magnitude or quantity of spherical aberration, and on the sign of spherical aberration. As described hereinbelow, negative spherical aberration may provide better depth of focus, and may therefore provide more desirable presbyopia mitigation capabilities.

Referring now to FIG. 5, a simplified analytical model 120 of an eye can be useful in determining presbyopia-mitigating high-order spherical aberration. The model illustrated in FIG. 5 comprises a ZEMAX™ optical design software model developed using software commercially available from ZEMAX Development Corporation of San Diego, Calif. Model Eye 120 includes an anterior cornea 122, which may be modeled as an even aspheric surface with a single conic constant. In other words, model cornea 122 comprises an ellipsoid with even order radial terms added to make it an aspheric surface. The radial terms used may comprise up to $8^{th}$ order for the anterior cornea. Central curvature, conic constant, and coefficients of the radial aspheric terms may be variables in model 120, so that the spherical aberration of the eye can be varied by adjusting these parameters.

Using the eye model 120, encircled energy, modulation transfer function (MTF) at a chosen frequency, and geometrical point spread function (PSF), can be computed to estimate image quality for different spherical aberrations and object distances. Polychromatic calculations can be performed using a plurality of wavelengths of light, often using three or more wavelengths of light, such as 0.45 microns, 0.55 microns, and 0.65 microns light. Weighting factors of 0.04, 1, and 0.35 may be applied to the wavelengths specified above, respectively. While pupil size may be varied in some analyses, at least some of the calculations described below were done with a single 6 mm entrance pupil size, with the imaged object being positioned on the optical axis of the model eye.

Figure 6:
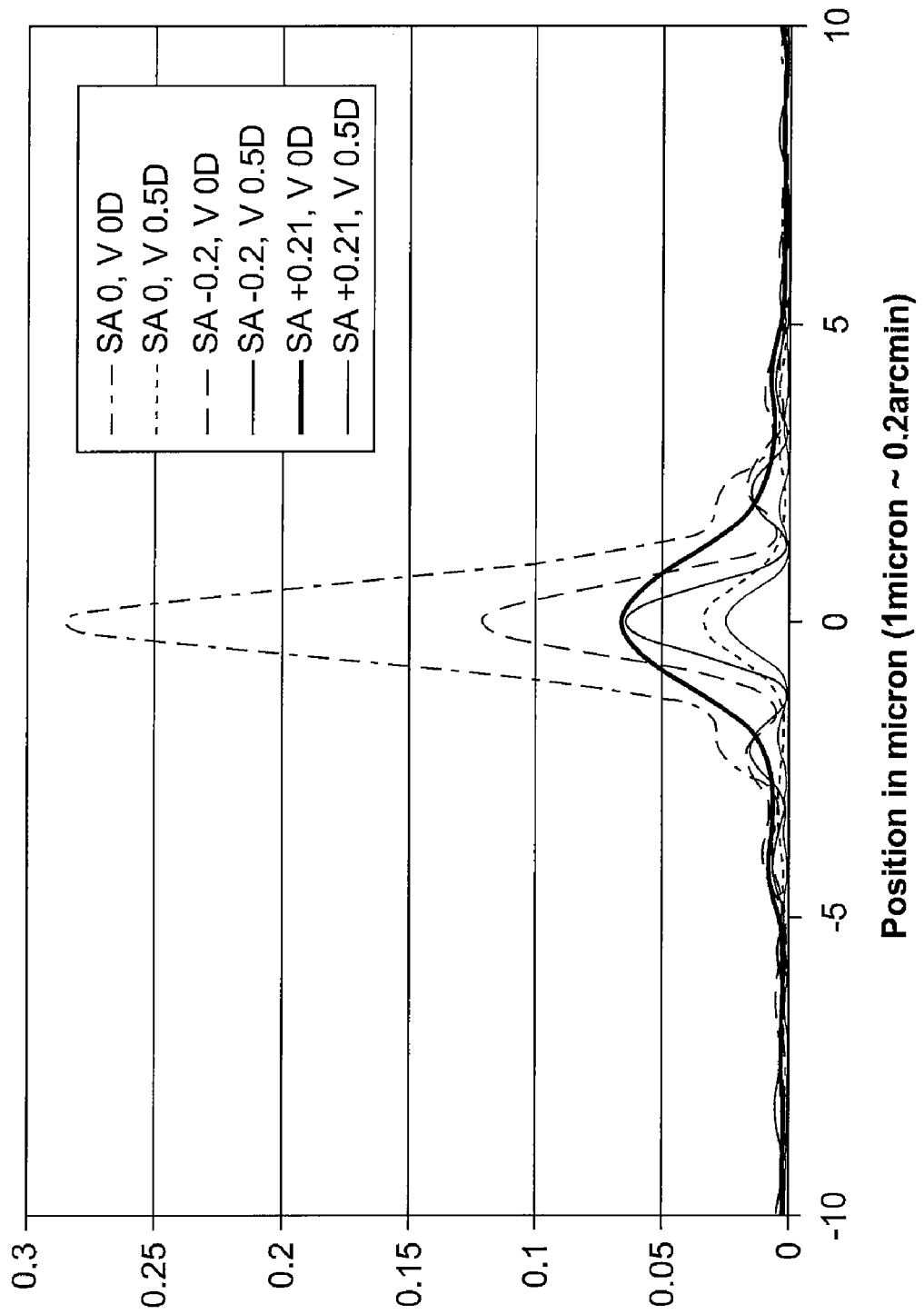
FIG. 6 graphically illustrates geometrical point spread function (PSF) values for differing spherical aberrations at differing viewing distances, as calculated with the model of FIG. 5.

Referring now to FIG. 6, geometrical pointspread functions were calculated with the model eye of FIG. 5 at differing spherical aberrations SA. An object, and specifically a light point source, was modeled at an infinite distance (V=0D) and at 2 meters (V=0.5D) from the eye in which V is the vergence. FIG. 6 graphically represents a cross section of the geometric point spread function for the model eye with a spherical aberration SA of about zero, of −0.2 microns, and of +0.21 microns. In the graph of FIG. 6, the horizontal or x axis represents the position in microns on the retina, with the distances measured from the optical axis of the eye. One micron length on the retina subtends to approximately 0.2 arc minutes of angle at the center of the corneal lens.

The geometric point spread function (PSF) peak is highest for the case in which little or no spherical aberration is present and the object is at an infinite distance. However, the pointspread function of this model eye spreads rapidly as the object comes closer to the eye, with the substantially zero spherical aberration model at a 0.5D vergence having a much lower peak height. In contrast, the change in peak height with changes in vergence is significantly smaller for the model eye having negative spherical aberration (SA –0.2, V0D/0.5D). Along with the reduction in peak height change, the model eye with negative spherical aberration has a point spread function which stays more localized as the object moves from an infinite distance to 2 meters (on other words, as vergence V changes from 0 to 0.5D).

Figure 7:
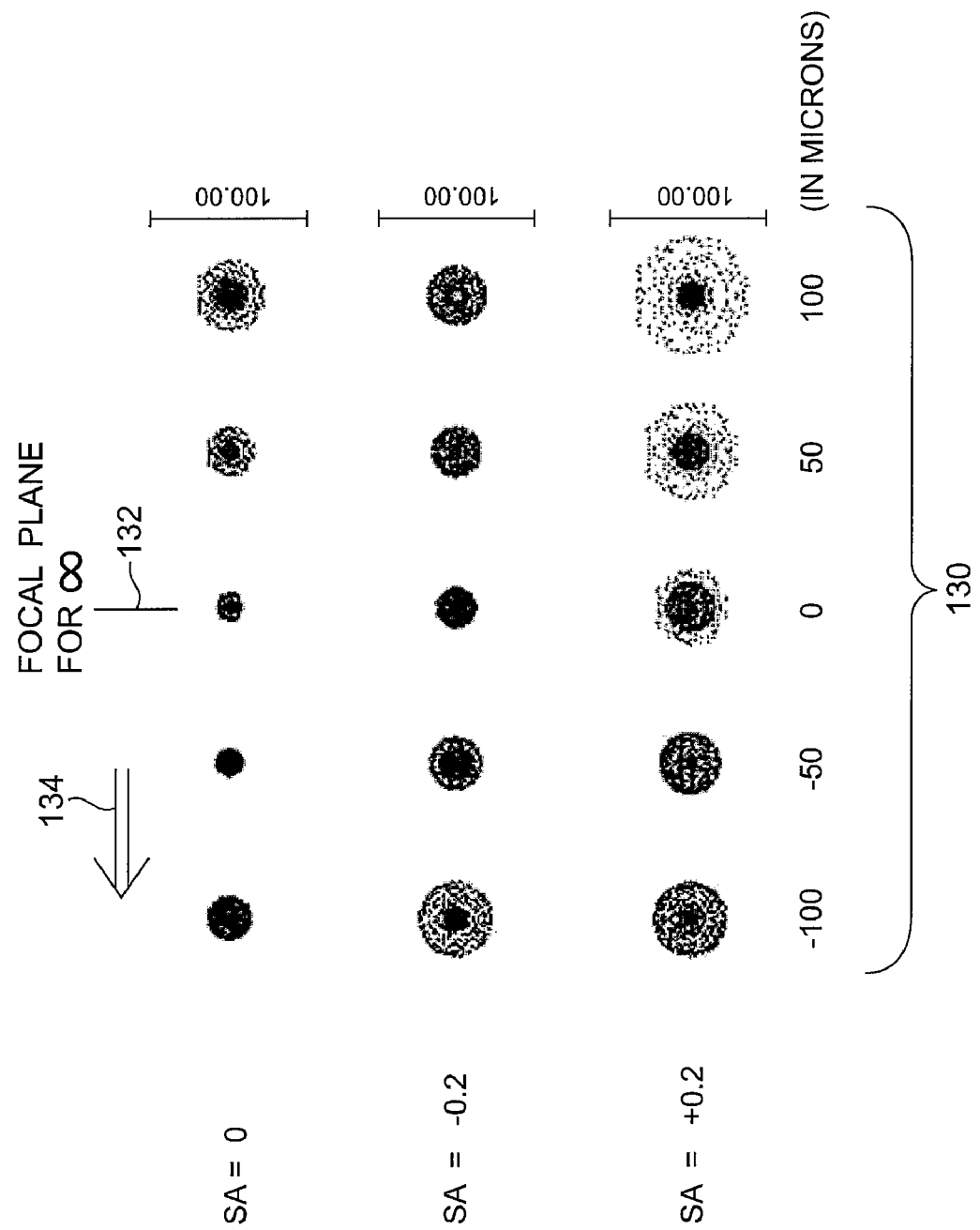
FIG. 7 graphically illustrates a comparison of through focus spot diagrams for eyes having differing spherical aberrations at differing focal distances.

Referring now to FIG. 7, an array of through focus spot diagrams 130 graphically illustrates images of a point source when the eye has varying amounts of spherical aberration and the image plane is at varying distances from the cornea. Through focus spot diagrams are provided for an eye having little or no spherical aberration, SA=0; an eye having negative spherical aberration, SA=–0.2; and an eye having positive spherical aberration SA=+0.2. The numbers appearing along the bottom of the array 130 indicate a distance along the optical axis at which the associated through focus spot diagrams are analyzed, with the "0" position being at the best focus point, typically located at the retina R (as indicated by the best focal plane for infinity 132). Positive numbers to the right side of the array indicate distances farther from the cornea as measured from the best focus point, while the negative numbers on the left side of the array represent positions closer to the corneal lens of the eye model. As a point source moves from infinity closer to the eye, the image at the retina (for an eye without accommodation) will change in the direction of arrow 134. Thus, the image of the point source formed at the retina would be a spot diagram more to the left side of the central spot. The measurements indicated are in microns.

As indicated along the top of the array, the best focus spot size is smallest for the SA=0 case. Note that for negative spherical aberration, the spot diagrams include a relatively high intensity central region on the left side of the array (at imaging distances closer to the cornea than the best paraxial focus point), while this same model has spot diagrams which spread out more evenly on the right side of the array (at greater distances from the best paraxial focus point). This characteristic is reversed in the case in which spherical aberration is positive, with the spot having an intense central region on the right side of the array (at greater distances), while the positive spherical aberration results in even spreading of the spot at nearer focal distances toward the left side of the array.

Having a relatively intense central region with a dim peripheral tail may create a sharper image as compared to a spot diagram having an even distribution or a higher intensity at the periphery of the spot. Additionally, having an intense central spot at focal distances in front of the retina (closer to the cornea and/or along the left side of the array of FIG. 7) may be useful. More specifically, when an object moves closer to such an eye, the image on the retina is sharper. Additionally, the eye may be able to accommodate (using any residual accommodation) so as to focus an even sharper image onto the retina. The image of close objects is less sharp if a point source generates an intense central spot which is located posteriorly of the retina. Hence, the negative spherical aberration through focus spot diagrams across the middle row of array 130 appear to provide benefits by providing a long depth of focus, as any accommodative abilities remaining in the eye can assist the patient in bringing the intense central regions into focus. Furthermore, the change in retinal spot size (with varying distances) with such negative spherical aberration may be less than for the positive spherical aberration case, and/or than corresponding substantial changes in spot size of the zero spherical aberration case.

Figure 8:
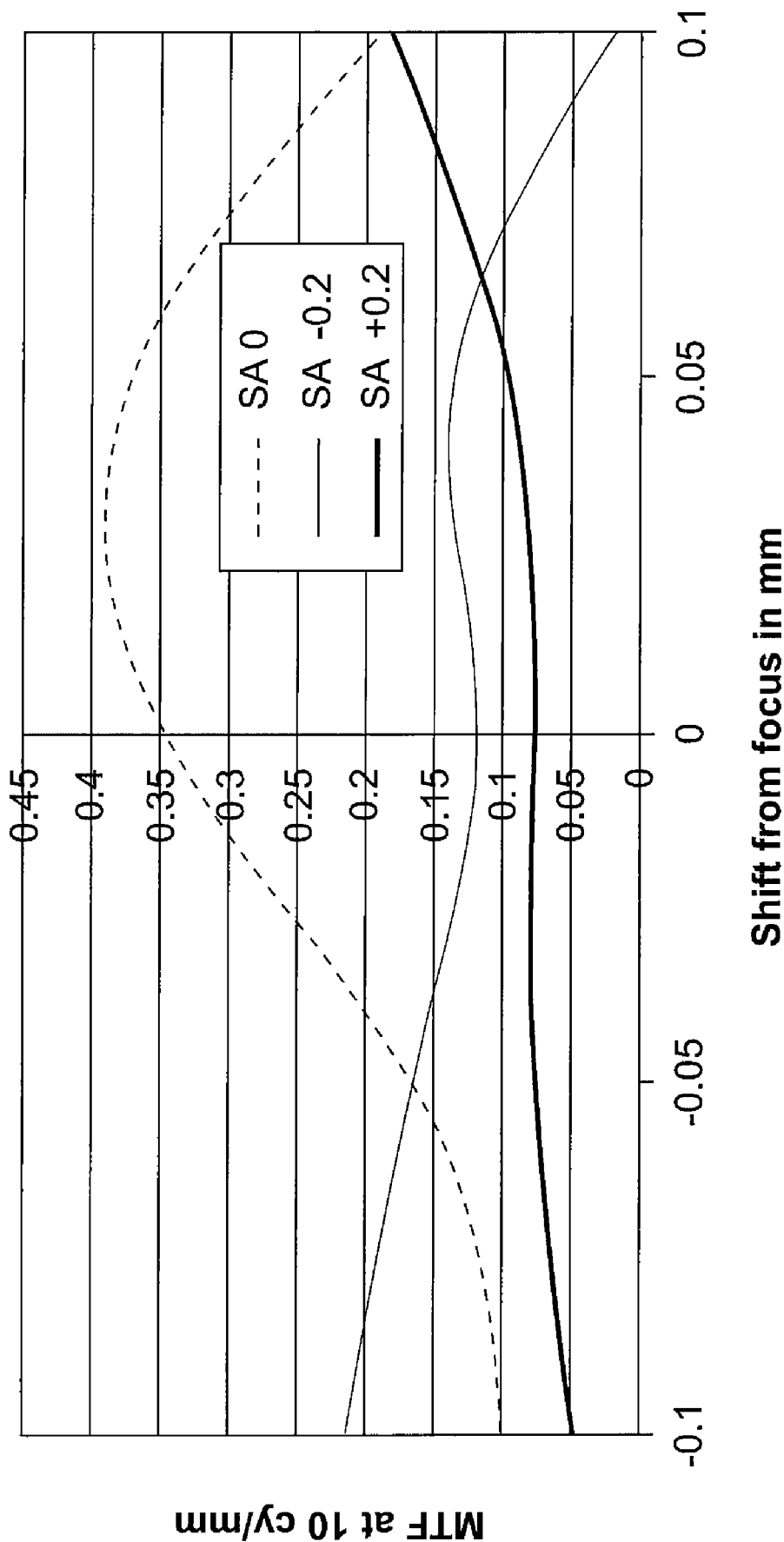
FIG. 8 graphically illustrates modulation transfer function (MTF) values as a function of shift from the focus for differing spherical aberrations.

Referring now to FIG. 8, the modulation transfer function (MTF) at 50 cycles/mm is shown as a function of distance from the focus. As was the case with the through focus spot diagrams of FIG. 7, the modulation transfer function may be highest at about the focus for the zero spherical aberration case. However, for distances which are less than the focus (and again closer to the cornea, here again having negative values along the x axis), the MTF for the model eye having a negative spherical aberration increases and actually exceeds the modulation transfer function value for the zero spherical aberration case when the shift from best focus is greater than 50 microns.

Assuming an eye has no accommodation (effectively having a fixed lens), if an object is placed at infinity and moves closer to the eye, the image location or focus will move away from the cornea and/or away from the retina. This may imply that a position of the retina may be closer to the cornea than the best image location. In other words, the retina may be located at a negative shift distance from the focus as the object is placed closer to the eye. In such situations, the MTF of the negative spherical aberration eye may be better than the substantially zero spherical aberration eye or the positive spherical aberration eye, as the modulation transfer function changes more slowly and stays at a moderate (and often acceptable) level when objects move closer to the eye.

Figure 9:
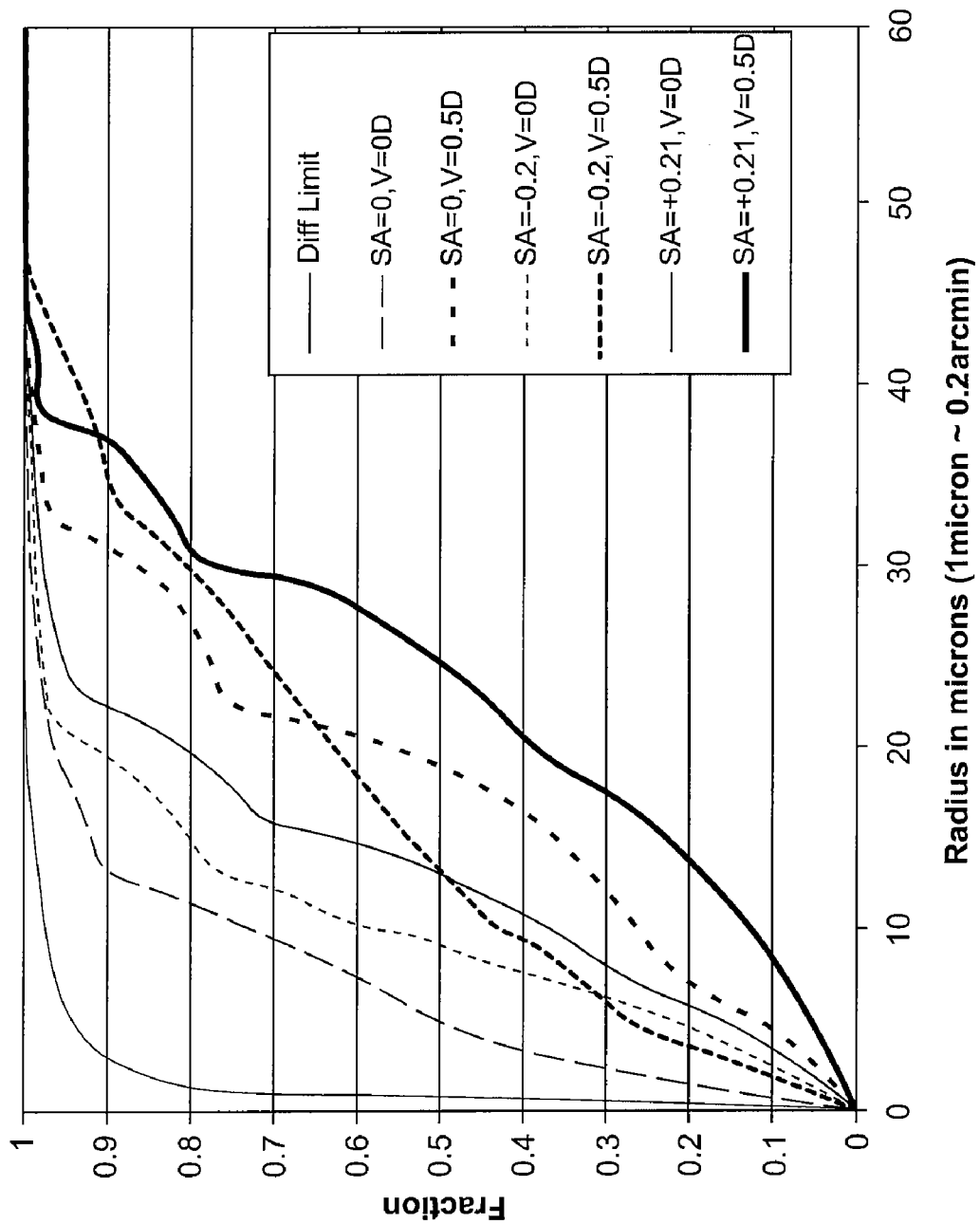
FIG. 9 graphically illustrates encircled energy values for differing spherical aberrations and object positions.

Referring now to FIG. 9, encircled energy for different spherical aberrations (SA again being specified in microns) and object positions (again being specified in vergence with V=0 being an object at infinity and V+0.5D being an object at 2 meters from the eye) are shown. This encircled energy graph indicates that an appropriate quality of negative spherical aberration may provide benefits similar to those described above regarding the PSF and the MTF. More specifically, the graphical data of FIG. 9 shows plots of geometric encircled energy calculated for polychromatic point sources placed on the optical axis at the indicated vergence distances. For comparison, a graph of a diffraction limited optical system is also shown. Per FIG. 9, as an object is moved from infinity to 2 meters, the radius to encompass a given fraction of the total energy increases. The change in the radius is smaller when the spherical aberration is negative, and is greater when the spherical aberration is positive.

The above indicates that an eye having an appropriate negative spherical aberration can provide a greater depth of focus. Hence, such negative spherical aberration may be beneficial to the eye to achieve mitigation of presbyopia and provide better vision despite changes in viewing distances. The above simulation data on pointspread functions, modulation transfer functions, and encircled energy support the ability of negative spherical aberration to alleviate the limited viewing depth of presbyopia. Each of these image quality characteristics showed smaller variation as an object position is shifted from infinity to somewhere closer to the eye when the eye has an appropriate negative spherical aberration, as opposed to a positive spherical aberration or substantially no spherical aberration. Any remaining residual accommodation of the eye may further enhance image quality factors for an eye having negative spherical aberration.

The Table illustrated in FIG. 10 shows an example of shape parameters of an initial or basic cornea and a corrected or treated cornea (both as modeled using an optical model similar to that of FIG. 5). Once again, the negative spherical aberration identified in FIG. 10 is assumed to be introduced through negative asphericity of the cornea, such as might be imposed by laser eye surgery, a contact lens, or the like. The coefficients shown in the table of FIG. 10 are standard Zernike polynomial coefficients, and the optimized coefficient values have been specified so as to enhance the benefit of the negative spherical aberration in the optical matrix described above. The amount of negative spherical aberration was changed to derive a shape that provided desirable characteristics on the optical matrix described above. The MTF and PSF, as described above, were utilized for this optimization.

Referring now to FIG. 11, a result of the optimization shows values of modulation transfer function at 50 cycles/mm for different object distances. The modulation transfer function was calculated geometrically, and the values are for polychromatic light with a 4 mm pupil size.

The values given in FIG. 11 indicate that a drop in the modulation transfer function as an object is moved away from the best focus location is much slower for the optimized cornea than for a standard cornea. The slower change in modulation transfer function implies a greater depth of field for the eye treated with the optimized shape of FIG. 10. The effect of 1.0 D reading glasses are also shown.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A method for treating presbyopia of a patient having an eye, the eye having a cornea and a retina, the method comprising:
   inducing a presbyopia-mitigating quantity of high-order negative spherical aberration in the eye to form an altered eye, wherein the altered eye has a negative spherical aberration and forms an image, in a plane between the cornea and the retina, of a point source at a viewing distance from the treated eye, wherein said image has a central area with a central intensity surrounded by a peripheral area with a peripheral intensity, the central intensity being higher than the peripheral intensity; and
   sharpening the image using residual accommodation of the eye.

2. The method of claim 1, wherein the presbyopia-mitigating quantity is in a range from about 0.05 to about 0.4 microns of negative spherical aberration across the pupil.

3. The method of claim 2, wherein the presbyopia-mitigating quantity is in a range from about 0.1 to about 0.3 microns of negative spherical aberration across the pupil.

4. The method of claim 3, wherein the presbyopia-mitigating quantity is in a range from about 0.15 to about 0.25 microns of negative spherical aberration across the pupil.

5. The method of claim 1, wherein the spherical aberration comprises a radially symmetric negative spherical asphericity.

6. The method of claim 5, wherein the spherical aberration correspond to at least one high order Zernike polynomial coefficient.

7. The method of claim 6, wherein the spherical aberration consists of a plurality of high order Zernike polynomial coefficients.

8. The method of claim 7, further comprising combining the spherical aberration with a plurality of wavefront Zernike coefficients, the wavefront Zernike coefficients defining a refractive defect-correcting prescription for the eye, and wherein the combined presbyopia-mitigating quantity of spherical aberration and refractive defect-correcting prescription are induced in the eye by at least one of reshaping a cornea, inserting a lens into the eye, positioning a lens in front of a cornea, laser eye surgery, LASEK, LASIK, photorefractive keratectomy, a contact lens, a scleral lens, an intraocular lens, a phacik intraocular lens, or a combination thereof.

9. The method of claim 1, further comprising
   measuring refractive aberrations of the eye with a wavefront aberrometer;
   determine wavefront Zernike coefficients of the measured refractive aberrations; and
   defining a prescription for the patient by combining the wavefront Zernike coefficients with at least one high-order Zernike coefficient corresponding to the presbyopia-mitigating quantity of spherical aberration.

10. The method of claim 1, further comprising:
    identifying the presbyopia-mitigating quantity of spherical aberration; and
    determining a presbyopia prescription providing the identified quantity of spherical aberration;
    wherein the presbyopia-mitigating quantity of spherical aberration is induced by superimposing the determined presbyopia prescription on the eye.

11. A method for treating presbyopia in a patient having an eye with a cornea and a retina, the method comprising altering refraction of the eye so that the altered eye has a negative spherical aberration in a range from about 0.1 to about 0.3 microns; and
    wherein a point source disposed at a viewing distance from the treated eye, is imaged by the altered eye to a plane between the cornea and the retina, and said image has a central area with a central intensity surrounded by a peripheral area with a peripheral intensity, the central intensity being higher than the peripheral intensity, so that the presbyopia is mitigated.

12. A system for treating presbyopia of an eye, the eye having a cornea and a retina, the system comprising:
    a prescription generator module coupled to an output, the prescription generator module defining a presbyopia-mitigating quantity of high-order negative spherical aberration for the eye, such that the eye has an induced negative spherical aberration and such that the eye images a point source, when the point source is disposed at a viewing distance from the treated eye, to a plane between the cornea and the retina, and such that the image has a central area with a central intensity surrounded by a peripheral area with a peripheral intensity, the central intensity being higher than the peripheral intensity, the output configured for communication to a lens producing or eye modifying assembly, wherein the prescription generator has an input;
    a wavefront system coupled to the input of the prescription generator, the wavefront system generating a plurality of refractive Zernike coefficients corresponding to sensed aberrations of an eye; and
    the lens producing or eye modifying assembly, including an ablative laser beam for imposing a prescription on the eye by directing a pattern of laser energy toward a cornea of the eye;

wherein the prescription generator combines the refractive Zernike coefficients with at least one presbyopia-mitigating Zernike coefficient, the at least one presbyopia-mitigating Zernike coefficient comprising at least one high-order Zernike coefficient corresponding to the presbyopia-mitigating quantity of spherical aberration, so as to provide the eye with between about 0.1 and about 0.3 microns of negative spherical aberration across the pupil.

* * * * *